United States Patent [19]

Gilbert

[11] 4,247,724
[45] Jan. 27, 1981

[54] PROCESS FOR PREPARING HEXANITROBIBENZYL

[75] Inventor: Everett E. Gilbert, Morristown, N.J.

[73] Assignee: The United States of America as represented by the Secretary of the Army, Washington, D.C.

[21] Appl. No.: 79,128

[22] Filed: Sep. 26, 1979

[51] Int. Cl.³ .............................................. C07C 79/10
[52] U.S. Cl. .................................................. 568/931
[58] Field of Search ............... 568/924, 927, 930, 931, 568/932

[56] References Cited

PUBLICATIONS

Shipp et al., J. Org. Chem., vol. 31, pp. 857 to 861 (1966).

*Primary Examiner*—Leland A. Sebastian
*Attorney, Agent, or Firm*—Nathan Edelberg; Robert P. Gibson; A. Victor Erkkila

[57] ABSTRACT

2,2′, 4,4′, 6,6′-hexanitrobibenzyl, an intermediate compound used for making hexanitrostilbene, is prepared by dissolving trinitrotoluene in a solvent system comprising a water-immiscible solvent and an aliphatic alcohol and then adding a metal hypochlorite solution containing a metal hydroxide to the trinitrotoluene solution to form the hexanitrobibenzyl. The compound is then separated from the reaction mixture.

9 Claims, No Drawings

4,247,724

PROCESS FOR PREPARING HEXANITROBIBENZYL

GOVERNMENTAL INTEREST

The invention described herein may be manufactured, used and licensed by or for the Government for Governmental purposes without the payment to me of any royalties thereon.

BACKGROUND OF THE INVENTION

The present invention relates to a novel process for the preparation of 2,2',4,4',6,6'-hexanitrobibenyl (HNB). This compound when reacted with an alkaline metal hypochlorite will form the compound 2,2',4,4',6,6'-hexanitrostilbene, an important thermally-stable explosive which is also useful as a nucleating agent promoting a desired mode of crystallization of trinitrotoluene.

Up until the present invention, the preferred method for preparing HNB was described in U.S. Pat. No. 3,505,413 and in a paper by Shipp and Kaplan, *Journal of Organic Chemistry*, 31, 857 (1966). The references teach dissolving trinitrotoluene (TNT) in a solvent mixture comprising one part tetrahydrofuran and two parts methanol by volume. A solution of sodium hypochlorite, which is made alkaline by the addition of sodium hydroxide is then slowly added to the solution of TNT. During the addition of the sodium hypochlorite to the solution of TNT, the temperature did not exceed 35° C. After a suitable aging period (15 minutes), the crystalline material was filtered and then washed with methanol and dried. It is reported that the amount of crude HNB obtained is 79% of theoretical.

The prior art process, while effective, does have a decided disadvantage in requiring the use of large volumes of solvent mixtures, which include expensive compounds. U.S. Pat. No. 3,505,413 explains that the solvent should be one which will dissolve TNT at ambient temperatures and below and which, with the addition of a lower aliphatic alcohol, will provide a homogenous solution with an alkaline metal hypochlorite. Examples of such solvents are tetrahydrofuran, p-dioxane, diglyme and acetonitrile, which are all water-miscible materials.

Also, in accordance with the prior art process, the temperature at which the reaction proceeds must be kept low in order to minimize undesired side reactions between TNT and alkali as well as the competing reacton of the solvent system. The Shipp et al. paper suggests temperatures under 15° C.

Unlike the prior art process, it has now been discovered that HNB can be prepared by using a solvent system which is relatively inexpensive and will permit the reaction to proceed at temperatures higher than was originally thought possible and produce a crude HNB product of lighter color and greater purity.

SUMMARY OF THE INVENTION

Accordingly, an object of the present invention is to provide a process for producing HNB by dissolving TNT in an inexpensive solvent system and then reacting the dissolved TNT with an akaline metal hypochlorite.

Another object of the instant invention is to be able to allow the reaction to proceed without maintaining low temperatures.

These and other objects and advantages will be apparent in the detailed description to follow.

DETAILED DESCRIPTION OF THE INVENTION

In the practice of the present invention, TNT, a compound well known in the art, is dissolved in a solvent system comprising a water-immiscible solvent, as opposed to a water-miscible solvent, and an aliphatic alcohol.

The water-immiscible solvents which can be employed in the present invention are, for example, aromatic compounds such as benzene, toluene, chlorobenzene and nitrobenzene; halogenated aliphatic hydrocarbons such as methylene chloride and ethylene dichloride; lower alkyl esters such as ethyl acetate; lower alkyl ketones such as methyl ethyl ketone; acetals such as dimethoxymethane (methylal) and 1,1,diethoxyethane.

When referring to lower alkyls, it is meant a lower alkyl of 1–4 carbon atoms such as methyl, ethyl, propyl and butyl. Other water-immiscible solvents can be used as will be well recognized by those skilled in the art. The only limitation is that the solvent be capable of dissolving TNT when combined with the aliphatic alcohol at temperatures up to about 60° C. and not react preferentially with a metal hypochlorite. In this connection solvents such as methyl formate, nitromethane and 2,4-pentadione are inoperative in the present process because they will preferentially react with the metal hypochlorite. The aliphatic alcohols employed in the present process can be such materials as methanol, ethanol, propanol and butanol.

In preparing the solvent system, the ratio by volume of the water-immiscible solvent to the aliphatic alcohol is from 1:2 to 1:8 and preferably from 1:5 to 1:8. The amount of solvent mixture necessary per gram of TNT is about 5 mls to about 10 mls. This is significantly less solvent than is necessary in the prior art process where 15 mls per 1 gram of TNT is suggested.

To increase the solubility and increase the rate in which the TNT will go into solution, the solvent mixture is heated to temperatures from about 40° C. to about 60° C. This can be done prior to or after adding the TNT. The temperature may also be adjusted after the reaction begins by utilizing the heat of reaction to raise the temperature and thus insure total solubilization of the TNT. After the TNT is in solution, a dilute aqueous solution of metal hypochlorite made alkaline by the addition of an alkaline metal hydroxide is slowly added, e.g. during 5 to 15 minutes, while mixing to form HNB according to the following reaction scheme.

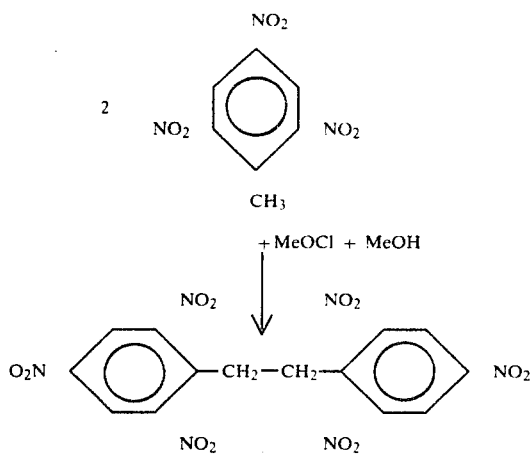

In the above reaction scheme MeOCl is a metal hypochlorite and MeOH is a metal hydroxide. The symbol Me denotes an alkali metal, such as sodium, potassium and lithium, or an alkaline earth metal such as magnesium, strontium, calcium and barium. The solution of metal hypochlorite may be of any convenient concentration but dilute solutions of about 5% to about 15% by weight being readily available are preferred. Although the use of the alkaline metal hypochlorite solution is preferred, organic reagents such as alkyl hypochlorite may be used in lieu thereof. An example of such compounds is tertiary butyl hypochlorite. To insure the correct reaction scheme, from about 0.25 to about 0.75 mole and preferably about 0.5 mole of alkali metal or alkaline earth metal hydroxide is added per mole of the metal hypochlorite.

In accordance with the present invention, after the hypochlorite solution is added to the TNT solution the reaction proceeds immediately and the HNB can be filtered from the solution without delay. Alternatively, the reaction can be allowed to proceed for a suitable aging time, for example, 15 minutes. The temperatures at which the reaction can proceed are from about 35° C. to about 50° C. and preferably from 40° C. to 45° C. The filtered HNB is then washed in methanol and dried. Yields of 70% of the theoretical yield and better can be obtained.

The following examples will more fully illustrate the embodiments of the invention. Unless otherwise specified, all parts and percentages are by weight.

EXAMPLE I 10 grams of 2,4,6-trinitrotoluene (TNT) is added to a solvent mixture containing 10 mls of benzene and 80 mls of methanol. The mixture is then heated to 40° C. to attain a solution of the TNT. 35 mls of a 5% sodium hypochlorite solution containing 0.5 gram of sodium hydroxide is added dropwise to the TNT solution while stirring and maintaining the solution between 35° C. to 40° C. The reaction mixture is then stirred for 30 minutes and filtered. The precipitate is then washed with methanol and dried to yield 7.5 grams (75% of theoretical) of HNB having a melting range of 212° C. to 218° C. and light color.

EXAMPLE II

Following Example V of U.S. Pat. No. 3,505,413, 10 grams of TNT is dissolved in a solvent system comprising 50 mls of tetrahydrofuran (THF) and 100 mls of methanol. 100 mls of a 1.8% sodium hypochlorite solution containing 0.5 grams of NaOH is added to the TNT solution over a period of 5 to 10 minutes in order to control the temperature so as not to exceed 35° C. The reaction mixture is allowed to stand for 15 minutes and the precipitate is then filtered from the solution, washed thoroughly with methanol and dried. The yield of HNB is 7.9 grams (79% of theoretical).

When the Shipp, Kaplan process is repeated using 50 mls of acetonitrile as the cosolvent in place of the THF, the yield is 59% of theoretical. The materials obtained have a melting range of about 195° C. to 205° C. and are purple brown in color. Shipp and Kaplan reported a melting range of 218° C. to 220° C. for recrystallized HNB.

The product obtained in accordance with the present invention is light in color with melting ranges higher than that obtained in the Shipp, Kaplan process. Accordingly, a less crude product can be obtained with the present process.

EXAMPLE III

The process of Example II is repeated but 50 mls of benzene is used in place of the THF. The process produced 5.0 grams (50% of theoretical) of HNB having a light color and a melting range of 212° C. to 218° C.

EXAMPLE IV 5 grams of TNT is dissolved in a solvent system comprising 5 mls of benzene and 25 mls of methanol. 14.5 mls of a 5% sodium hypochlorite solution containing 0.2 gram of sodium hydroxide is slowly added to the TNT solution. The temperature of the reaction is from 39° C. to 41° C. The precipitate is then immediately filtered from the reaction mixture, washed in methanol and dried to yield 3.5 grams (70% of theoretical) of HNB having a melting range of 218° C. to 222° C. and a light color.

EXAMPLE V 5 grams of TNT is dissolved in a solvent system comprising 5 mls of toluene and 40 mls of methanol. 18 mls of a 5% sodium hypochlorite solution containing 0.25 gram of sodium hydroxide is slowly added to the TNT solution. The temperature of the reaction is from 35° C. to 40° C. The reaction mixture is then stirred for 30 minutes at about 30° C. to 40° C. and the precipitate filtered from the solution, washed in methanol and dried to yield 3.7 grams (74% of theoretical) of HNB having a melting point of 205° C. cl EXAMPLE VI The process of Example II is repeated but 50 mls of toluene is used in place of the THF. The process produces 3.6 grams of HNB (36% of theoretical) having a melting range of 212° C. to 218° C.

EXAMPLE VII 5 grams of TNT is dissolved in a solvent system comprising 5 mls of chlorobenzene and 25 mls of methanol. 14.5 mls of a 5% sodium hypochlorite solution containing 0.2 gram of sodium hydroxide is slowly added to the TNT solution. The reaction temperature is from 39° C. to 41° C. The precipitate is then immediately filtered, washed in methanol and dried to yield 3.5 grams (70% of theoretical) of HNB of light color having a melting range from 212° C. to 215° C.

EXAMPLE VIII

The process of Example II is repeated but 50 mls of chlorobenzene is used in place of the THF. The process produced 4.8 grams (48% of theoretical) of HNB having a melting range of 212° C. to 218° C.

EXAMPLE IX 5 grams of TNT is dissolved in a solvent system comprising 5 mls of nitrobenzene and 40 mls of methanol. 18 mls of a 5% sodium hypochlorite solution containing 0.25 gram of sodium hydroxide is slowly added to the TNT solution. The reaction mixture is then stirred for 30 minutes and the precipitate is filtered from the solution, washed in methanol and dried to yield 3.6 grams (72% of theoretical) of HNB having a light color and a melting range of 210° to 216° C.

EXAMPLE X

The process of Example II is repeated but 50 mls of nitrobenzene is used in place of THF. The process produced 3.2 grams (32% of theoretical) of HNB having a light color and a melting range of 220° C. to 225° C.

EXAMPLE XI 5 grams of TNT is dissolved in a solvent system comprising 5 mls of ethyl acetate and 25 mls of methanol. 14.5 mls of a 5% sodium hypochlorite solution containing 0.2 gram of sodium hydroxide is slowly added to the TNT solution. The reaction temperature is from 45° C. to 50° C. The precipitate is then immediately filtered from the reaction mixture, washed in methanol and dried to yield 3.9 grams (78% of theoretical) of HNB having a light color and a melting range of 199° C. to 206° C. This process was repeated six more times under slightly varied conditions using ethyl acetate as the cosolvent. The yields were all in the range of 78% to 81% of theoretical.

EXAMPLE XII 5 grams of TNT is dissolved in a solvent system comprising 5 mls of methyl ethyl ketone and 40 mls of methanol. 18 mls of a 5% sodium hypochlorite solution containing 0.25 gram of sodium hydroxide is added to the TNT solution. The reaction temperature is from 35° C. to 40° C. The reaction mixture is stirred for 30 minutes and then the precipitate is filtered, washed in methanol and dried. The yield is 3.6 grams (71% of theoretical) of HNB having a melting range of 200° C. to 208° C.

EXAMPLE XIII 5 grams of TNT is dissolved in a solvent system comprising 5 mls of methylene chloride and 25 mls of methanol. 14.5 mls of a 5% sodium hypochlorite solution containing 0.20 gram of sodium hydroxide is added to the TNT solution. The reaction is run at temperatures of 50° C. to 55° C. to insure solubility of the TNT in the mixture. It will be noted that although the reaction is run at temperatures above the boiling point of methylene chloride (40° C.) there is only negligible loss of the solvent because of the excessive amount of methanol present. The precipitate is then immediately filtered, washed in methanol and dried to yield 4.0 grams (80% of theoretical) of HNB having a melting range of 206° C. to 212° C.

EXAMPLE XIV 5 grams of TNT is dissolved in a solvent system comprising 10 mls of ethylene dichloride and 25 mls of methanol. 14.5 mls of a 5% sodium hypochlorite solution containing 0.2 gram of sodium hydroxide is added to the TNT solution. The reaction is run at 45° C. to insure solubility of the TNT in the mixture. The precipitate is then immediately filtered, washed in methanol and dried to yield 3.8 grams (75% of theoretical) of HNB having a melting range of 207° C. to 212° C.

EXAMPLE XV

Example II is repeated but 50 mls of ethylene dichloride is substituted for THF. The process produces 5.2 grams (52% of theoretical) of HNB having a melting range of 212° C. to 218° C.

EXAMPLE XVI 5 grams of TNT is dissolved in a solvent system comprising 5 mls of methylal and 25 mls of methanol. 14.5 mls of a 5% sodium hypochlorite solution containing 0.2 gram of sodium hydroxide is slowly added to the TNT solution. The reaction is run at 45° C. to insure solubility. The precipitate is then immediately filtered, washed in methanol and dried to yield 3.9 grams (78% of theoretical) of HNB having a melting range of 201° C. to 208° C.

This invention has been described with respect to certain preferred embodiments and various modifications. Variations in the light thereof will be suggested to persons skilled in the art and are to be included within the spirit and purview of this application and the scope of the appended claims.

I claim:

1. A process for preparing 2,2',4,4',6,6'-hexanitrobibenzyl comprising the steps of adding an aqueous solution of an alkali metal or alkaline earth metal hypochlorite containing an alkali metal or alkaline earth metal hydroxide to a trinitrotoluene solution in a solvent system comprising a water-immiscible solvent and an aliphatic alcohol and then recovering said hexanitrobibenzyl from the reaction mixture, said solvent system being capable of dissolving TNT at temperatures up to 60° C. and not reacting preferentially with the alkaline metal hypochlorite.

2. A process as defined in claim 1, wherein the said reaction takes place at temperatures of about 35° C. to about 50° C.

3. A process as defined in claim 1, wherein the water-immiscible solvent is selected from the group consisting essentially of benzene, toluene, chlorobenzene, nitrobenzene, methylene chloride, ethylene dichloride, ethyl acetate, methyl-ethyl ketone, 1,1,diethoxyethane and methylal.

4. A process as defined in claim 1 or claim 3, wherein the aliphatic alcohol is selected from the group consisting of methanol, ethanol, propanol and butanol.

5. The process as defined in claim 1, wherein the alkaline metal hydroxide is sodium hydroxide.

6. The process as defined in claim 1, wherein the concentration of the aqueous alkaline metal hypochlorite is from about 5% to about 15% by weight.

7. The process as defined in claim 1, wherein 0.25 mole to 0.75 mole of the metal hydroxide is added per mole of the metal hypochlorite.

8. The process as defined in claim 1, wherein from about 5 mls to about 10 mls of the solvent system is used for each gram of TNT.

9. The process as defined in claim 1, wherein the ratio by volume of the water-immiscible solvent to the aliphatic alcohol is from 1:2 to 1:8.

* * * * *